US011376196B2

(12) United States Patent
Ribani et al.

(10) Patent No.: US 11,376,196 B2
(45) Date of Patent: Jul. 5, 2022

(54) FILLING MACHINE

(71) Applicant: I.M.A. INDUSTRIA MACCHINE AUTOMATICHE S.P.A., Ozzano Dell'Emilia (IT)

(72) Inventors: Massimo Ribani, Ozzano Dell'Emilia (IT); Maurizio Bedetti, Ozzano Dell'Emilia (IT); Alessandro Masotti, Ozzano Dell'Emilia (IT); Lorenzo Maldina, Ozzano dell'Emilia (IT)

(73) Assignee: I.M.A. INDUSTRIA MACCHINE AUTOMATICHE S.P.A., Ozzano Dell'Emilia (IT)

( * ) Notice: Subject to any disclaimer, the term of this patent is extended or adjusted under 35 U.S.C. 154(b) by 96 days.

(21) Appl. No.: 16/760,614

(22) PCT Filed: Oct. 30, 2018

(86) PCT No.: PCT/IB2018/058494
§ 371 (c)(1),
(2) Date: Apr. 30, 2020

(87) PCT Pub. No.: WO2019/087066
PCT Pub. Date: May 9, 2019

(65) Prior Publication Data
US 2021/0177700 A1    Jun. 17, 2021

(30) Foreign Application Priority Data

Oct. 31, 2017  (IT) .......................... 102017000123930

(51) Int. Cl.
*B65B 1/06*    (2006.01)
*A61J 3/07*    (2006.01)
(Continued)

(52) U.S. Cl.
CPC ................. *A61J 3/074* (2013.01); *B65B 1/06* (2013.01); *B65B 1/32* (2013.01); *B65B 3/003* (2013.01);
(Continued)

(58) Field of Classification Search
CPC .......... A61J 3/074; A61J 3/07; A61J 2200/74; A61K 9/48; A61K 9/4833; B65B 1/06;
(Continued)

(56) References Cited

U.S. PATENT DOCUMENTS 5,796,051 A * 8/1998 Chiari ..................... G01G 17/00
                                                          177/17
5,852,259 A * 12/1998 Yanase ................... G01G 17/00
                                                          177/145
(Continued)

FOREIGN PATENT DOCUMENTS

| CN | 1324314 | 11/2001 |
|----|---------|---------|
| CN | 1551753 | 12/2004 |

(Continued)

OTHER PUBLICATIONS

Examination Report dated Jun. 16, 2021 in corresponding Indian Patent Application No. 202027017659.
(Continued)

*Primary Examiner* — Nicolas A Arnett
(74) *Attorney, Agent, or Firm* — Wenderoth, Lind & Ponack, L.L.P.

(57) ABSTRACT

A filling machine for filling capsules a product comprises a plurality of operative stations for carrying out operations on the capsules, a movement device provided with seats for housing and moving the capsules through the operative stations; and a weighing station to weigh of the capsules and comprising a weighing unit and a transfer system to transfer the capsules from the movement device to the weighing unit
(Continued)

and vice versa. The weighing unit comprises a gripping element coupled with a weighing cell and provided with a housing for receiving and holding the capsule to be weighed. The transfer system include a first transfer element to remove the capsule from the seat of the movement device and insert it in the housing to measure its weight, and a second transfer element to remove the body from the housing and insert it in the seat of the movement device, after the measurement.

12 Claims, 5 Drawing Sheets

(51) Int. Cl.
    *B65B 1/32*    (2006.01)
    *B65B 3/00*    (2006.01)
    *B65B 3/28*    (2006.01)
    *A61K 9/48*    (2006.01)

(52) U.S. Cl.
    CPC .............. *B65B 3/28* (2013.01); *A61J 2200/74* (2013.01); *A61K 9/4833* (2013.01); *Y10S 53/90* (2013.01)

(58) Field of Classification Search
    CPC ... B65B 1/32; B65B 3/003; B65B 3/28; Y10S 53/90
    See application file for complete search history.

(56) References Cited

U.S. PATENT DOCUMENTS

| | | | |
|---|---|---|---|
| 6,425,422 B1* | 7/2002 | Trebbi | A61J 3/074 141/67 |
| 6,837,280 B2 | 1/2005 | Ragazzini et al. | |
| 7,210,507 B2 | 5/2007 | Facchini | |
| 7,328,559 B2 | 2/2008 | Gamberini | |
| 7,726,102 B2 | 6/2010 | Gamberini | |
| 8,266,874 B2 | 9/2012 | Runft et al. | |
| 8,350,164 B2 | 1/2013 | Wang | |
| 9,021,772 B2 | 5/2015 | Bedetti | |
| 9,170,213 B2* | 10/2015 | Runft | B65B 3/003 |
| 9,255,824 B2 | 2/2016 | Runft et al. | |
| 9,995,618 B2 | 6/2018 | Boehringer et al. | |
| 2004/0172925 A1 | 9/2004 | Ragazzini et al. | |
| 2005/0217752 A1 | 10/2005 | Facchini | |
| 2007/0062164 A1 | 3/2007 | Gamberini | |
| 2008/0219803 A1 | 9/2008 | Runft et al. | |
| 2008/0256906 A1 | 10/2008 | Gamberini | |
| 2009/0014086 A1* | 1/2009 | MacMichael | B65B 1/24 141/12 |
| 2011/0108470 A1 | 5/2011 | Wang | |
| 2011/0259468 A1 | 10/2011 | Bedetti | |
| 2011/0277871 A1 | 11/2011 | Trebbi et al. | |
| 2013/0206484 A1 | 8/2013 | Consoli et al. | |
| 2013/0327791 A1 | 12/2013 | Runft et al. | |
| 2014/0311104 A1 | 10/2014 | Gamberini et al. | |
| 2015/0204714 A1 | 7/2015 | Boehringer et al. | |
| 2020/0408585 A1* | 12/2020 | Wick | G01G 17/00 |

FOREIGN PATENT DOCUMENTS

| | | |
|---|---|---|
| CN | 102227201 | 10/2011 |
| CN | 103108807 | 5/2013 |
| DE | 10 2005 057 393 | 5/2007 |
| EP | 2 370 044 | 3/2013 |
| EP | 2 851 060 | 3/2015 |
| EP | 2 851 303 | 3/2015 |
| WO | 2010/070592 | 6/2010 |
| WO | 2016/200259 | 12/2016 |

OTHER PUBLICATIONS

International Search Report dated Jan. 15, 2019 in International (PCT) Application No. PCT/IB2018/058494.

* cited by examiner

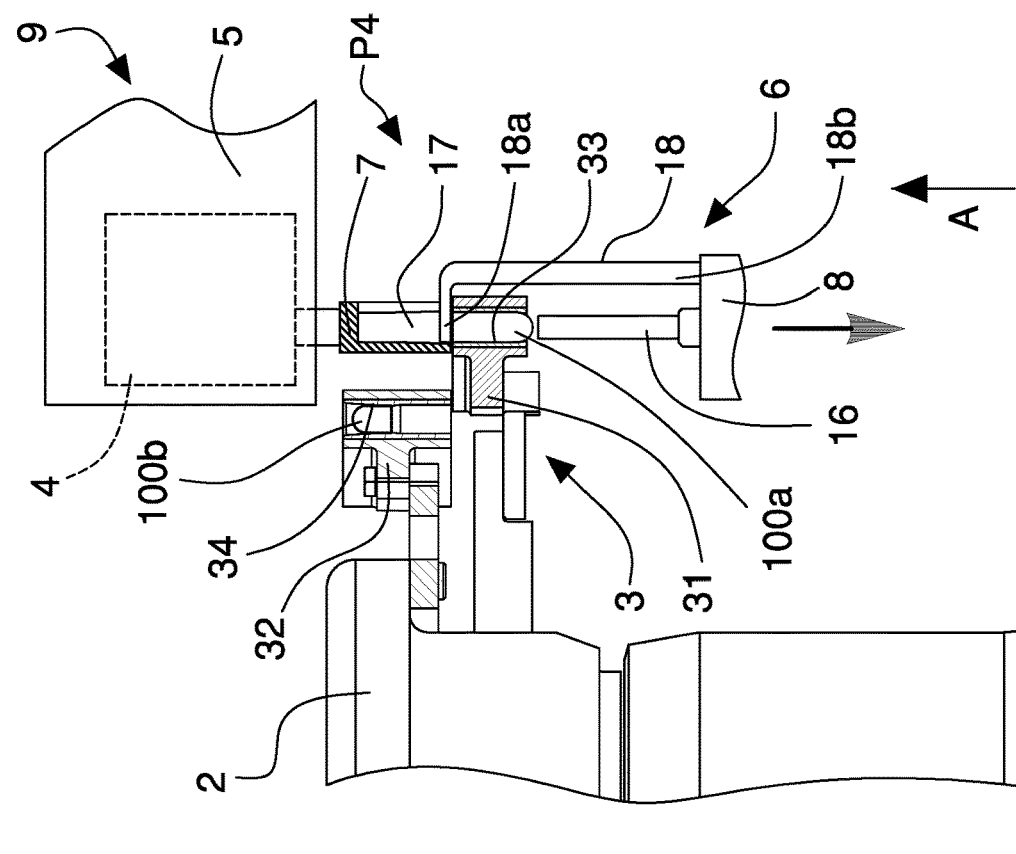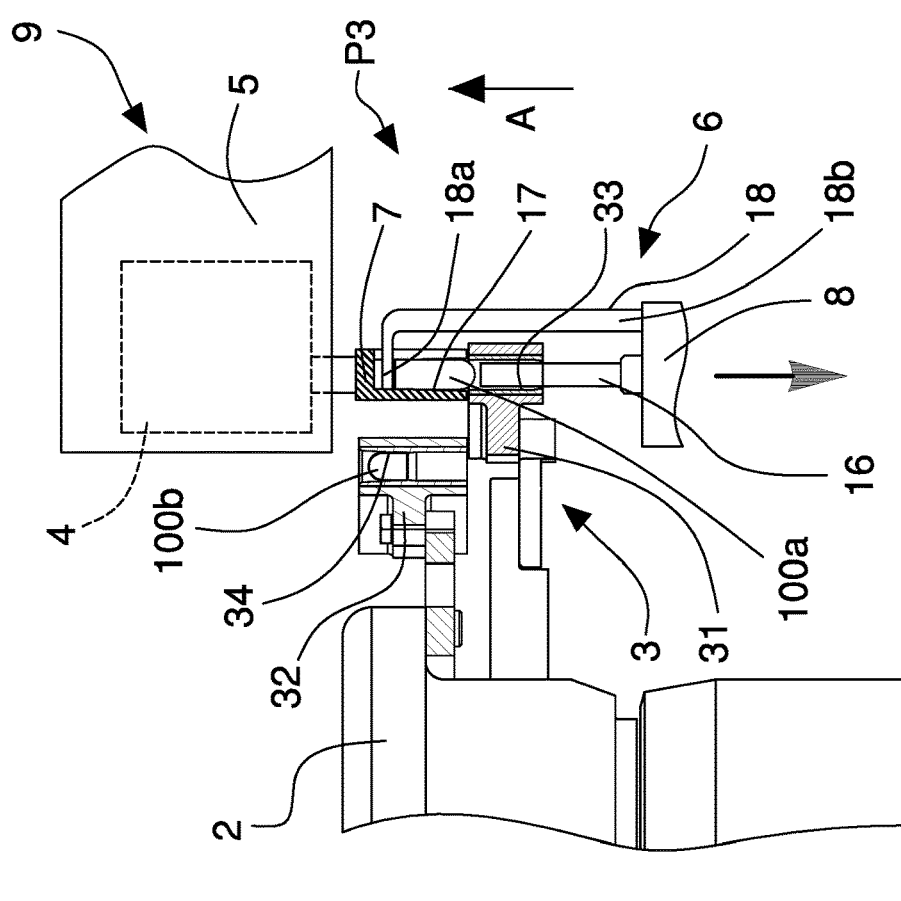

FILLING MACHINE

The present invention relates to automatic filling machines for filling capsules or casings or similar elements with products and it relates in particular to a filling machine provided with weighing systems adapted to measure the weight of the product or products dosed in the capsules.

In the filling processes of capsules with liquid, powder, granule, time-release products, tablets, etcetera it is known the use of weighing apparatuses or devices placed downstream of the filling machine or of a filling station of the latter for measuring the weight of the product dosed in the capsules.

The weight control is necessary to discard non-compliant capsules from production as they contain a quantity of product outside the admitted dosage tolerance field and for correcting possible excesses or errors in dosing the product, with feedback action on the filling machine or station. Especially in the pharmaceutical sector it is very important to verify that the quantity of the product dosed in the single capsules is exactly the required one, with very limited tolerance ranges.

Generally, a single weighing of capsules is carried out at the end of the dosing, as the empty capsule weight is known and is included within a definite tolerance range, indicated and guaranteed by capsule suppliers/manufactures. Thereby, it is possible to calculate the weight of the dosed product (net weight) with a certain degree of precision by subtracting the known weight of the empty capsule (tare) from the weight measure of the filled capsule (gross weight).

However, in the filling processes wherein the quantity of product to be dosed in capsules is very small, for example of few milligrams, (so called "microdoses") and the required tolerance range of the product dosage is limited, for example ±10%, normal weight variations of empty capsules greatly affect and influence the weight measurement. In fact, as the weight of the empty capsules is comparable with that of the dosed product, such weight variations can be wider than the tolerance field of the admitted dosage. In such a case controlling only the filled capsule weight is not sufficient to guarantee that the dosed quantity of product is within the requested limits and it is necessary to previously weigh the empty capsule and calculate by difference the weight of the dosed product.

They are therefore known solutions providing a first weighing station, upstream of the filling machine or of the filling station, which measures the empty capsule weight (tare), and a second weighing station, downstream of the filling machine or of the filling station, which measures the weight of filled capsules (gross weight). The difference between the two measured weights allows to calculate precisely the net weight of the dosed product.

Weighing apparatuses carrying out such a type of direct measurement comprise electronic scales typically provided with a plurality of measuring cells or weighing cells, each of which is provided with a respective support (small plate) onto which the capsule must be placed for the time necessary to measure it correctly.

The weight control can be of total type, i.e. carried out on all the capsules filled by the filling station (so called 100% weight control) or a partial control, of statistical type, carried out on a sample of filled capsules, selected randomly.

In certain types of pharmaceutical production, control of all filled capsules is in any case required and, in general, such a solution is largely preferred by pharmaceutical companies in order to guarantee a better quality of the packed product.

It is known that, in order to carry out an accurate and precise weighing, using electronic scales, it is necessary an appropriate measuring time. In particular, a minimum time lapse must pass between the deposition of the capsule on the scales plate and the measuring of the weight thereof, necessary to allow the scales to stabilize i.e. to allow reduction of vibrations which generate when the capsule is laid down on the plate and to proceed with the detection of the weight.

In some known filling machines for carrying out a total weight control of the capsules it is provided to place electronic scales outside the machine and/or upstream and downstream of operative stations of the machine such as to measure primarily the weight of all empty capsules before they enter the machine (or the operativestations) and therefore of all the capsules filled with the product exiting from the machine (or from operative stations). With this configuration, providing a proper number of electronic scales and/or weighing cells, it is not necessary to reduce the filling machine productivity or speed to have a suitably long measuring time for a highly precise and accurate measurement.

While in function, in case the scales placed downstream of the filling machine detects non-compliant capsules, i.e. filled with a quantity of material outside the admitted tolerance range, the filling machine must be stopped to carry outa control and/or an adjustment of the filling station and all the capsules produced before the malfunction of the aforesaid filling station is detected and comprised between the latter and the weighing station must be discarded as they are probably non-compliant. As the scales is placed outside the filling machine, or in any case downstream of all the operative stations, the number of capsules to be discarded can be very high, according to the configuration and the dimensions of the filling machine. If the dosed pharmaceutical product is expensive, such a waste is not acceptable and it is necessary to proceed with complicated and time-consuming procedures for rescuing the product dosed in the discarded capsules.

There are also known filling machines comprising a weighing station placed immediately downstream of the filling station so as to reduce the number of capsules to be discarded in case of dosage errors.

In such a type of filling machine, proper transfer means are provided to take capsules from a movement or transport device of the machine and place them on the plates of the weighing cells and to return the capsules to the transport device after their weighing. The weighing operation—which comprises the transfer of the capsule from the transport device to the weighing cell or load cell, its weighing on the latter and its transfer from the weighing cell to the transport device—is carried out in one of the stop intervals of the intermittent motion whereby the filling machine moves.

In this case, the weight control of the total type is possible, but with a lower precision and accuracy than those obtainable in filling stations with the weighing station placed outside, as the time available for the weighing operation does not allow electronic scales to stabilize completely. Using a longer time interval, suitable for a more precise and accurate weighing, machine productivity or speed would result too low, having to increase the duration of the stop intervals of the intermittent motion. For this reason, in this type of filling machine a control of statistical type of the capsules weight is generally carried out, which does not require that the duration of stop intervals of the intermittent motion whereby the machine moves is the same as the time necessary to carry out the whole weighing operation.

An object of the present invention is to improve known filling machines arranged to fill capsules or casings or similar elements with products and to measure the weight of the products dosed in the aforesaid capsules.

Another object is to provide a filling machine able to carry out with high accuracy and precision a weight control of the total type, i.e. able to measure the weight of all the filled capsules, even at high functioning speeds of the machine.

Another object is to realize a filling machine which allows to verify the weight of all capsules immediately downstream of a filling station, so as to significantly limit the number of the capsules to be discarded following to a malfunctioning of the filling station detected by the weight measuring.

A further object is to realize a particularly compact and small sized filling machine and having reliable and safe functioning.

Such and other objects are achieved by a filling machine according to one of the following attached claims.

The invention shall be better understood and implemented referring to the enclosed drawings showing some exemplary and non-limiting embodiments, wherein:

FIGS. 2 to 5 are respective partial and enlarged sections of a movement device and of a weighing station of the filling machine of FIG. 1, in subsequent stages of an operative sequence of a capsule weighing;

Figure 1:
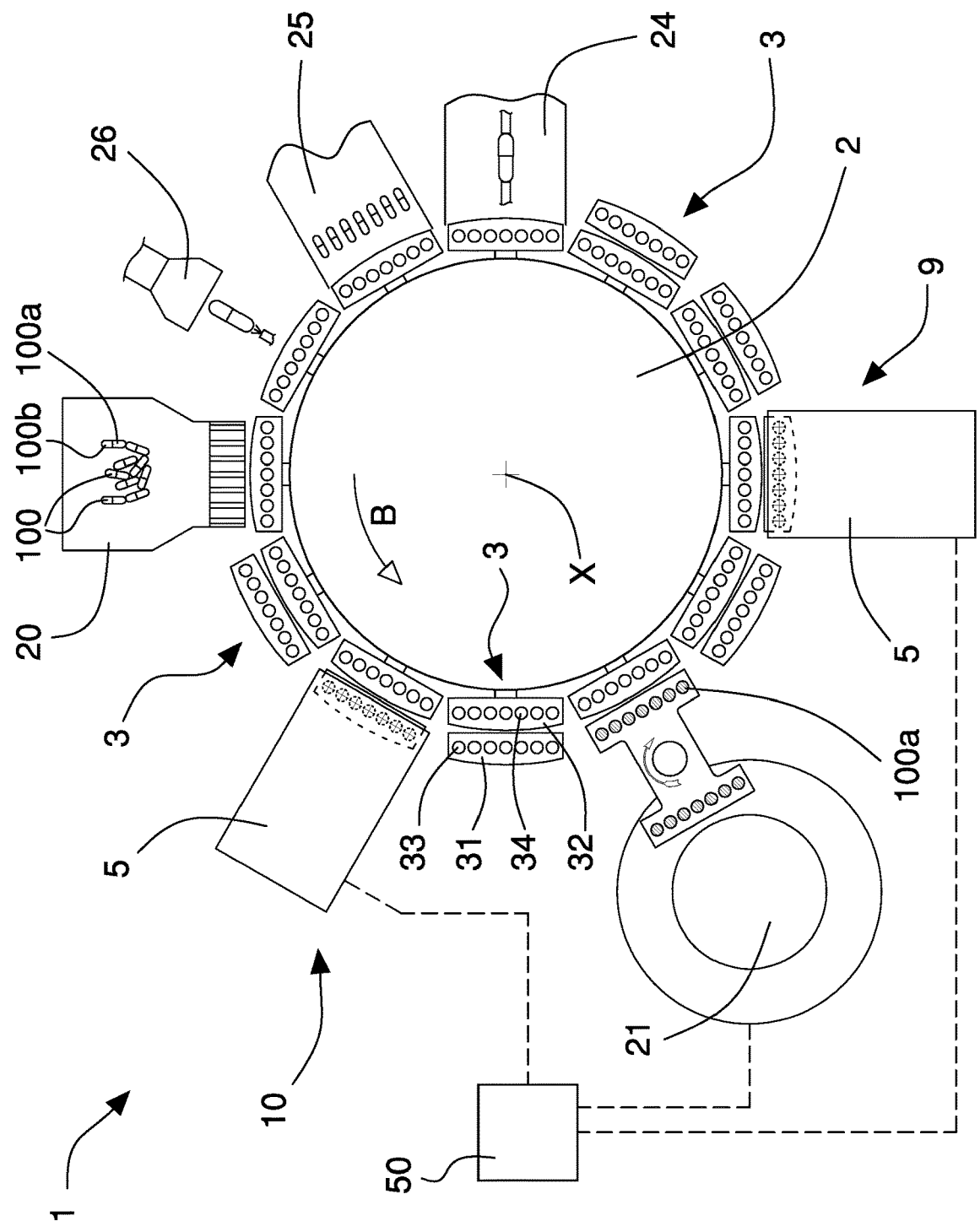
FIG. 1 is a plan schematic view from above of a capsule filling machine according to the invention.
Figure 3:
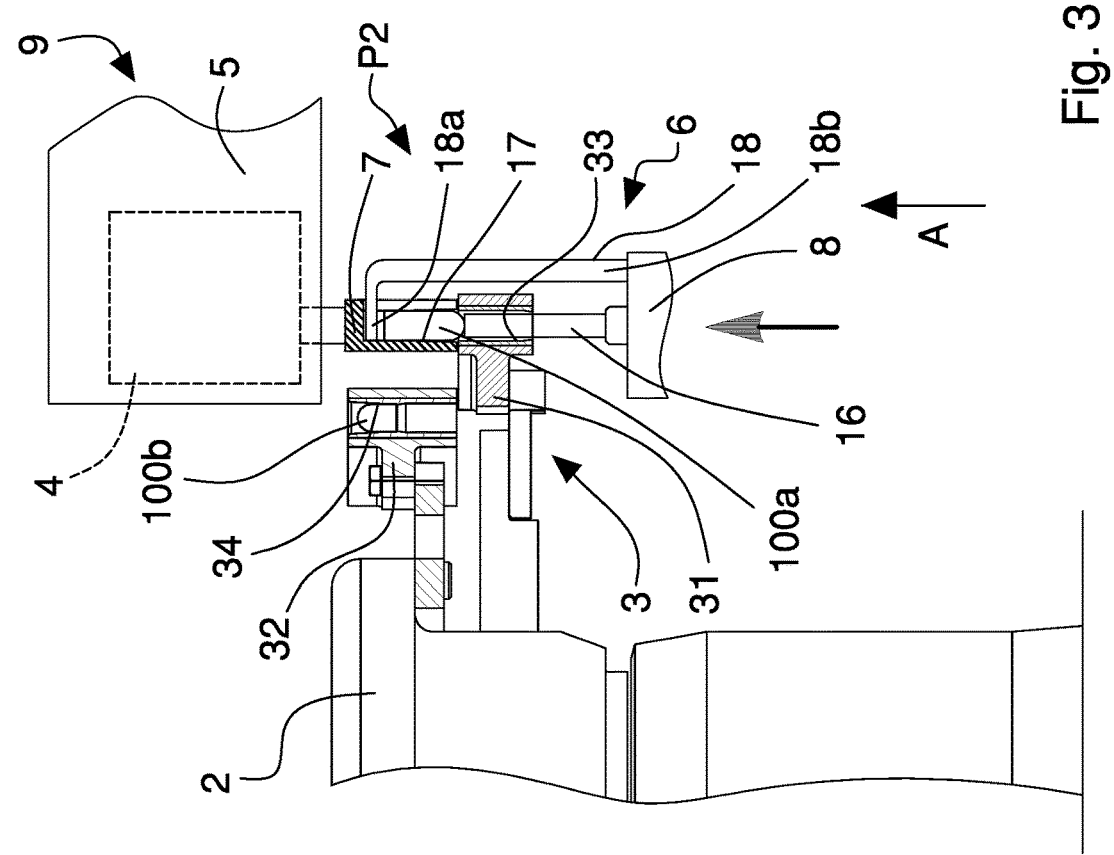
Figure 2:
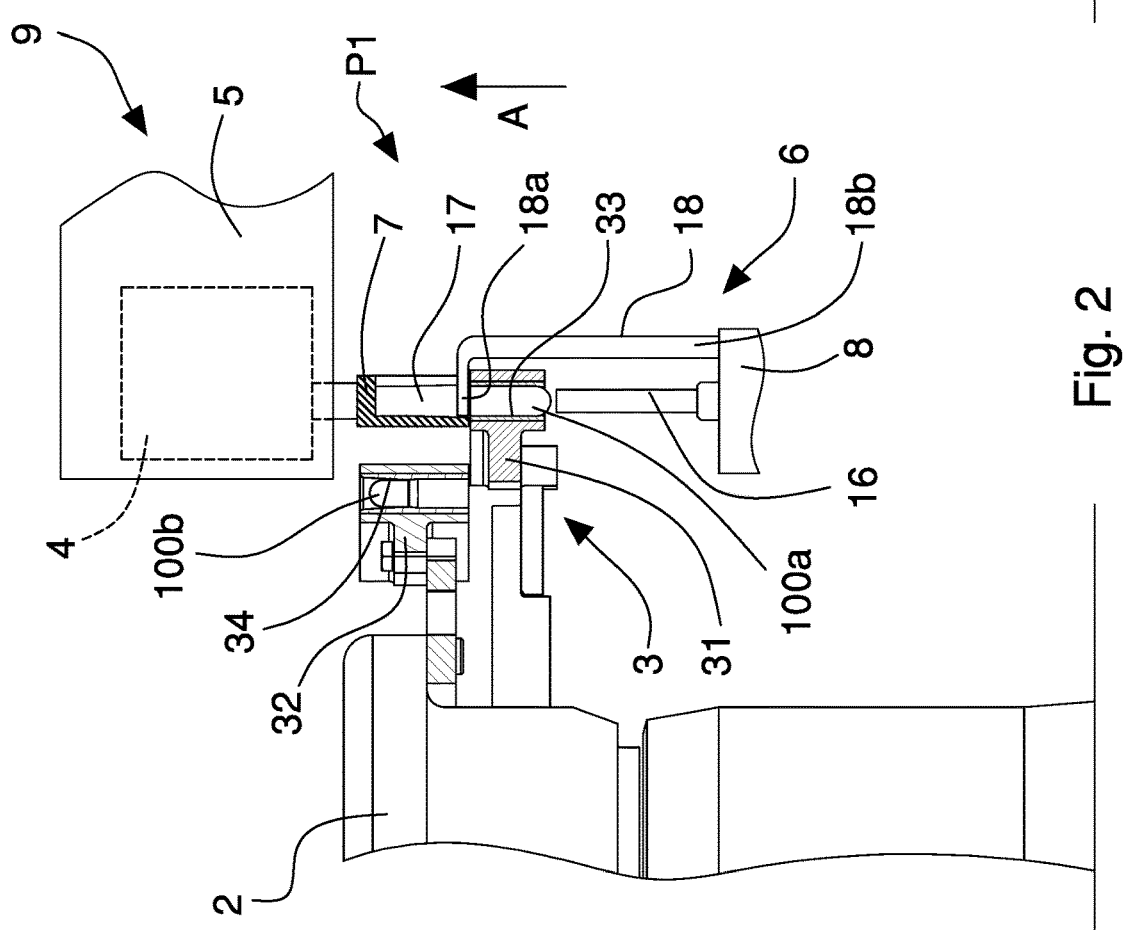

Referring to FIGS. 1 to 7, it is schematically illustrated a filling machine 1 according to the invention adapted to fill capsules 100, casings or similar elements, for example hard gelatine capsules, with a liquid, powder, granule, time-release product, tablets etcetera, in particular a pharmaceutical product. Each capsule 100 is formed by a body 100a and a cap 100b which can be temporarily uncoupled and separated to allow dosing the product in the body 100a.

The filling machine 1 comprises a plurality of operative stations 20-26 arranged to carry out operations on the capsules 100, a movement device 2 provided with a plurality of supports 3 with respective seats 33, 34 for housing and moving the capsules 100 in sequence through the operative stations 20-26, and at least one weighing station 9 for weighing capsules 100 or bodies 100a of the capsules 100.

The movement device 2, of the known type, comprises a carousel or board, rotatable about a vertical rotation axis X and provided with a plurality of supports 3 arranged angularly spaced apart along the periphery or a circumferential rim of the aforesaid carousel. Each support 3 is formed by a first supporting element 31, having a plurality of first seats 33 intended to house the bodies 100a of the capsules 100, and a second supporting element 32, having a plurality of second seats 34 intended to house the caps 100b of the capsules 100. The supporting elements 31, 32 have elongated shape and are movable with respect to each other between an overlaid position wherein the respective seats 33, 34 are aligned and overlaid for inserting or removing all the capsules 100 (i.e. with the caps 100b applied to the respective bodies 100a) and a staggered position wherein the first seats 33 containing the bodies 100a are accessible for allowing the dosing of the product.

The first seats 33 and second seats 34 of the supports 3 comprise respectively pass-through cavities, i.e. open at opposite ends, and having convergent shape and/or properly shaped for receiving and holding by force or interference coupling the bodies 100a and caps 100b of the capsules 100.

In the illustrated embodiment, the weighing station 9 is arranged to weigh bodies 100a of the capsules 100 and comprises a weighing unit 5 and transfer means 6 adapted to transfer the bodies 100a of the capsules 100 from the movement device 2 to the weighing unit 5 and vice versa.

For this purpose the filling machine 1 comprises among the plurality of operative stations 20-26 a supplying and opening station 20 of the capsules 100 whereby the latter ones are introduced in the filling machine 1, and the caps 100b are extracted and separated from their respective bodies 10as which can thus receive the product in a subsequent filling station 21. The bodies 100a and caps 100b are inserted and housed respectively into the first seats 33 and into the second seats 34 of the supports 3 of the movement device 2. A capsule-closing station 24 is provided for coupling the caps 100b with the respective bodies 100a and thus close the capsules 100 after filling and weighing.

It is also provided, as better explained in the hereinafter description, that the weighing station 9 is arranged for weighing all the capsules 100.

The weighing unit 5 of the weighing station 9 comprises at least one gripping element 7 which is connected to a respective weighing cell or load cell 4 of the aforesaid weighing unit 5 and is provided with a housing 17 suitable for receiving and holding by force or interference coupling a body 100a to be weighed. More precisely, the weighing unit 5 comprises a plurality of gripping elements 7, in equal number as the seats 33, 34 present on each support 3 of the movement device 2, and an equal number of load cells 4. Thereby, all bodies 100a housed in the first seats 33 of a first supporting element 31 of the support 3 can be weighed at the same time by the weighing unit 5.

The transfer means 6 are movable along a direction of extraction A, in particular almost vertical, and include at least a first transfer element 16 arranged to remove one respective body 100a from a respective first seat 33 of a support 3 of the movement device 2 and insert said body 100a, by forcing it, into the housing 17 to allow the load cell 4 to measure its weight.

The transfer means 6 further comprise at least a second transfer element 18 arranged for removing the body 100a from the housing 17 and inserting the body 100a into the respective first seat 33 of the movement device 2, after the weight of said body 100a is measured.

More precisely, the first transfer element 16 and the second transfer element 18 are movable along the direction of extraction A between a first operative position P1, wherein the aforesaid transfer elements 16, 18 are disengaged and spaced apart from the body 100a, housed in the respective first seat 33 of a support 3 of the movement device 2 such as not to interfere with the movement of the latter, a second operative position P2, wherein the first transfer element 16 has completely extracted the body 100a from the first seat 33 and has inserted it inside the housing 17 of the gripping element 7, a third operative position P3, wherein the transfer elements 16, 18 are disengaged and spaced apart from the body 100a housed and hold by force or interference in the housing 17 such as to allow the load cell 4 to measure its weight, and a fourth operative position P4, wherein the second transfer element 18 has completely extracted the body 100a from the housing 17 and inserted it inside the respective first seat 33.

In the illustrated embodiment, the transfer means 6 of the weighing station 9 comprise a plurality of first transfer elements 16 and a respective plurality of second transfer elements 18, equal in number as the seats 33, 34 of each support 3 of the movement device 2, so as to transfer at the same time all the bodies 100a housed in the first seats 33 into the housings 17 of the gripping elements 7 and vice versa.

The weighing unit 5 with the gripping element 7 is arranged above the movement device 2 and the housing 17 has a lower opening 17a that enables the transfer means 6 to insert into, or remove from said housing 17 the body 100a along the direction of extraction A. The lower opening 17a of the housing 17 has a blunted or rounded rim to ease the insertion of the body 100a.

Figure 7:
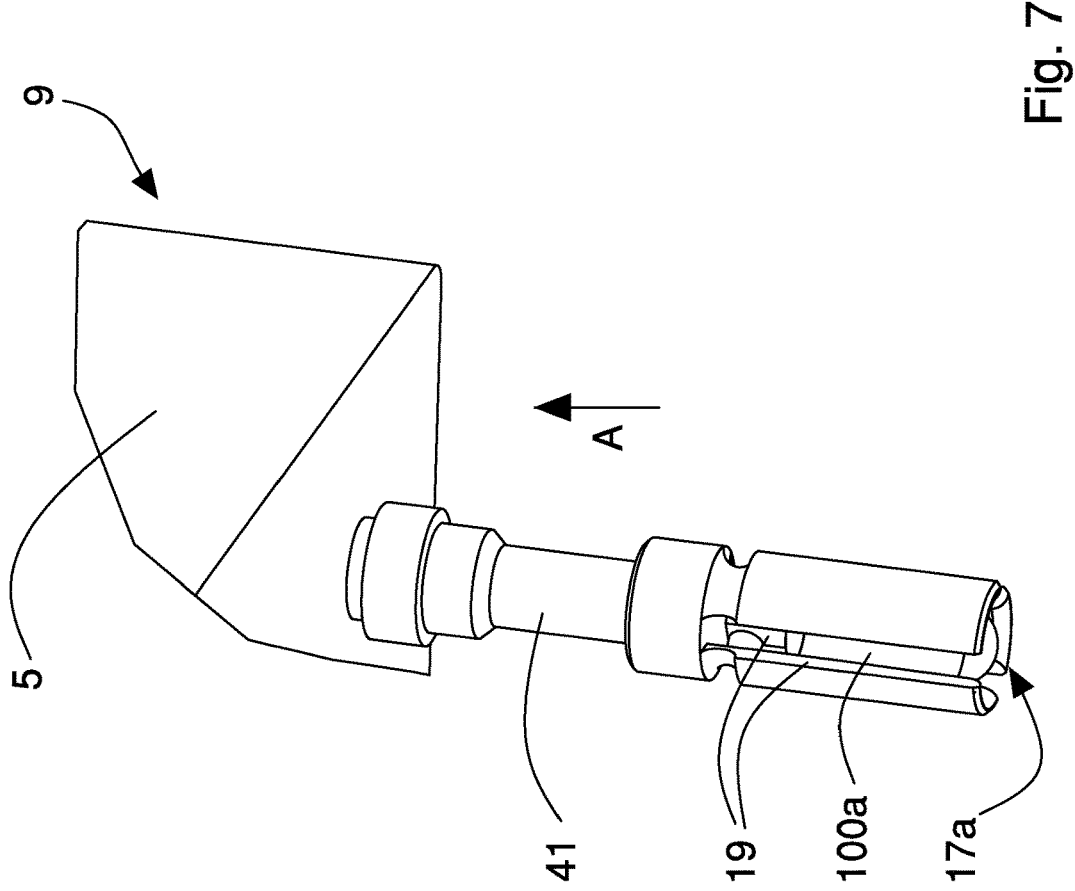
FIG. 7 is a perspective view of the gripping element of FIG. 6.
Figure 6:
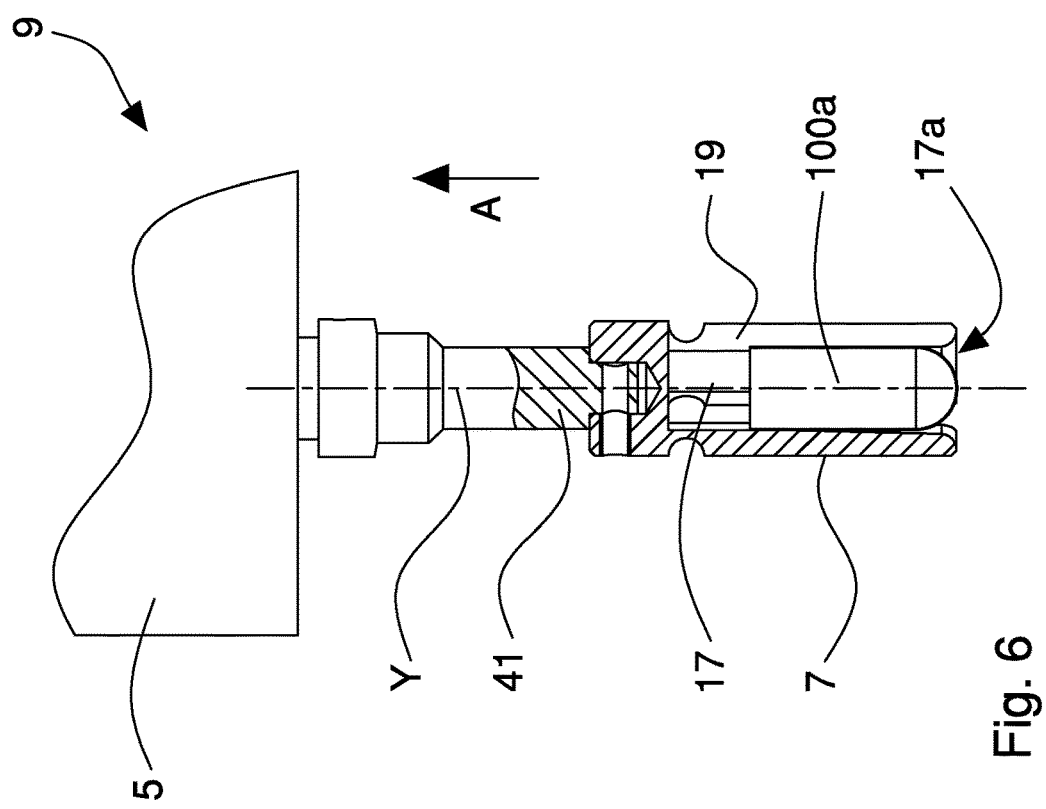
FIG. 6 is an enlarged and partial section of a gripping element of FIG. 2 associated to a body of a capsule.

As illustrated in particular in FIGS. 6 and 7, the housing 17 extends longitudinally, in particular parallel to the direction of extraction A, and has such an extension that it contains the body 100a or capsule 100. The housing 17 is also convergent or tapered starting from the lower opening 17a towards the load cell 4, as its internal cross-section (almost orthogonal to a longitudinal axis Y of the gripping element 7 which is parallel to the direction of extraction A) funnels gradually starting from the lower opening 17a to a smaller dimension of an external transverse dimension of the body 100a, or of the capsule 100. Thereby, once insertion is completed, the housing 17 is able to hold the body 100a by force or interference coupling. More precisely, the body 100a can be inserted and gradually pushed into the housing 17 wherein it stays reversibly fastened by virtue of the material elasticity (hard gelatine) it is made of and of its hollow shape. In the illustrated example, the capsule 100, the body 100a and the cap 100b have hollow cylindrical shape (the body 100a and the cap 100b are also provided with respective sphere-shaped bottoms) and the housing 17 has truncated-cone shape converging in the direction of the load cell 4, and circular inner transverse section.

The gripping element 7 is removably connected to a stem or plate 41 of the load cell 4, extending vertically from the weighing unit 5 downwards.

The first transfer element 16 has elongated shape and is arranged to be inserted, when moved along the direction of extraction A, inside a respective first seat 33 of a support 3 of the movement device 2 so as to abut onto the lower portion of the body 100a and therefore push the latter outside the first seat 33 inside the housing 17 along the direction of extraction A. More precisely, the first transfer element 16 is inserted into the first seat 33 through a lower opening of the latter so as to abut and push the body 100a to exit from the first seat 33 through an opposite upper opening of the latter.

The second transfer element 18 also has elongated shape and has at least one terminal end 18a adapted to abut onto an upper portion of the body 100a in order to push the latter outside the housing 17 and inside the first seat 33. More in detail, the second transfer element 18 substantially has upside down "L" shape and comprises a first elongated portion 18b, parallel to the direction of extraction A, and a second portion which is almost orthogonal to the first portion 18b and which forms the terminal end 18a.

The first transfer element 16 and the second transfer element 18 are fixed to a base element 8 of the transfer means 6 which is moved by action means, of the known type and not illustrated in the figures, along the direction of extraction A, between the different operative positions P1, P2, P3, P4.

The gripping element 7 also has one or more lateral opening 19, passing through and parallel to the direction of extraction A, which allow to insert and slide the terminal end 18a of the second transfer element 18 inside the housing 17 and along the direction of extraction A.

Referring in particular to FIG. 1, the filling machine 1 of the invention comprises a filling station 21 arranged to dispense and dose a product in the bodies 100a of the capsules 100; the weighing station 9 is placed downstream of the filling station 21, referring to a movement direction B of the capsules 100 in the filling machine 1, such as to measure the weight of bodies 100a containing the product.

The filling machine 1 also comprises a station of initial weighing 10 that is provided with a respective weighing unit 5 and with respective transfer means 6 and is placed upstream of the filling machine 21, with reference to the movement direction B, in such a way as to measure the weight of the empty bodies 100a. In such an embodiment of the filling machine 1 of the invention, the supplying and opening station 20, wherein the caps 100b were extracted and separated from the respective bodies 100a, is placed upstream of the station of initial weighing 10, while the capsule closing station 24, wherein the caps 100b are reapplied to the respective bodies 100a so as to reclose the capsules 100, is placed downstream of the weighing station 9.

The filling machine 1 of the invention further comprises a processing unit 50 connected to the weighing station 9 and to the station of initial weighing 10 and arranged to receive data about the measured weights and calculate an effective weight of the product dosed in each capsule 100 or respective body 100a and generate a warning signal in case of a non-compliant capsule or respective non-compliant body—as containing an amount of product having a weight outside the admitted tolerance field.

The plurality of operative stations 20-26 of the filling machine includes, furthermore, an exit station 25 wherein the capsules 100 filled with the product and compliant are extracted from the movement device 2 and conveyed outside the filling machine 1. The exit station 25 is connected to the processing unit 50 for receiving from the latter the warning signal and leave non-compliant capsules on the movement device 2. A discard station 26 is provided downstream of the exit station 25 to remove from the movement device 2 non-compliant capsules.

The filling station 21 is also connected to the processing unit 50 to receive therefrom the warning signal and stop such as to interrupt the filling of further capsules 100 which would result to be non-compliant.

The functioning of the filling machine 1 of the invention provides that closed capsules 100, i.e. having caps 100b coupled with respective bodies 100a, are introduced in the filling machine 1 in the supplying and opening station 20. In such a station, the bodies 100a and the caps 100b are separated and inserted respectively in the first seats 33 and in the second seats 34 of the supports 3 of the movement device 2.

The latter comprises a rotatable carousel rotating with intermittent motion about the rotation axis X such as to transfer the open capsules 100, i.e. having bodies 100a and caps 100b separated, through the subsequent operative stations 20-26 and weighing stations 9, 10.

In particular, in the station of initial weighing 10 the relative transfer means 6, in one of the stop stages of the intermittent motion, transfer the empty bodies 100a, contained in the first supporting element 31 of a support 3, in the respective gripping elements 7 of the weighing unit 5. More precisely, the first transfer elements 16 of the transfer means 6 are moved, together with the second transfer elements 18, from the first operative position P1 (FIG. 2) to the second operative position P2 (FIG. 3) such as to remove the bodies 100*a* from the respective first seats 33 and insert them, pushing them, into the respective housings 17 of the gripping elements 7. The transfer elements 16, 18 are hence moved into the third operative position P3 (FIG. 4) wherein they are disengaged and spaced from the body 100*a* housed and hold by force or interference in the housing 17 to allow the weighing cell 4 to measure the weight of the body 100*a*.

Once detection of the empty bodies 100*a* weight is over, the transfer elements 16, 18 are moved into the fourth operative position P4 such that the second transfer elements 18 can remove the bodies 100*a* from the housings 17 of the gripping elements 7 and insert them completely into their respective first seats 33 of the support 3.

Similarly to the weighing station 9 placed downstream of the filling station 21, the relative transfer means 6, in one of the stop stages of the intermittent motion, the transfer bodies 100*a*, filled with the product, from the first seats 33 of the support 3 into the housings 17 of the gripping elements 7 of the weighing unit 5.

The sequence of movements of the first transfer elements 16 and second transfer elements 18 of the transfer means 6 between the different and subsequent operative positions P1-P4 is the same as the previously described one for the station of initial weighing 10, in this case weighing cells 4 of the weighing units 5 of the weighing stations 9 measuring a weight of the bodies 100*a* containing the product.

It is worth noting that thanks to transfer means 6 and gripping elements 7 receiving and holding by force bodies 100*a* of the capsules 100 it is possible to transfer very rapidly, easily and efficiently the aforesaid bodies 100*a* from/to the movement device 2 and allow to weigh precisely and accurately by means of load cells 4, connected directly to the aforesaid gripping elements 7, the bodies 100*a*, both empty and containing the product. The first transfer elements 16 and second transfer elements 18 are in fact moved linearly along the direction of extraction A with short run, which can thus be carried out in short times, between the various operative positions P1-P4. Therefore, the time necessary to carry out the whole weighing operation—which comprises the transfer of the body 100*a* from the movement device 2 to the gripping element 7 of the load cell 4, the weighing thereof on the latter and transfer thereof from the gripping element 7 to the movement device 2- is very short and can be equal to the duration of the stop intervals of an intermittent motion of the filling machine 1 also having high rate or speed or productivity. In other words, thanks to the filling machine 1 of the invention it is possible to carry out a total weight control of the capsules 100 without reducing the functioning speed of the latter, which can thus be very high and the same as that of known filling machines which carry out a partial control of statistical type of capsules or a control of the total type but with limited precision and accuracy.

The processing unit 50 connected to the weighing station 9 and to the station of initial weighing 10 receives data relative to measured weights such as to calculate the effective weight of the product dosed in each body 100*a* and generate a warning signal in case of a non-compliant body 100*a*, as containing a quantity of product with a weight outside the admitted tolerance range. Such a warning signal is sent to the exit station 25, which keeps on the movement device 2 the non-compliant capsules intended to be removed from the latter in the following discard station 26.

As the weighing station 9 is placed immediately downstream of the filling station 21, in case an anomaly is detected in the filling i.e. a malfunction of the filling station 21 (highlighted by the measurement of a weight of the dosed product outside the admitted tolerance range), it is possible to interrupt immediately the filling of the bodies 100*a*, i.e. the functioning of the filling station 21 in order to reduce the number of non-compliant capsules to discard. In particular, the capsules to be discarded are only those contained in the supports 3 comprised between the filling station 21 and the weighing station 9, therefore a reduced number.

In one variant of the filling machine 1 of the invention non shown in the figures, it is provided that the weighing station 9 is placed downstream of the capsule closing station 24 and that the station of initial weighing 10 is placed upstream of a capsule opening station 100, i.e. interposed between the latter and the supplying station wherein the capsules are introduced into the filling machine 1. In this variant of the filling machine 1 of the invention, the transfer means 6 of the weighing stations 9, 10 transfer the capsules 100 respectively empty and filled with the product, from the movement device 2 to the gripping element 7 and vice versa, i.e. the weight of all the capsules 100 is weighed.

Figure 8:
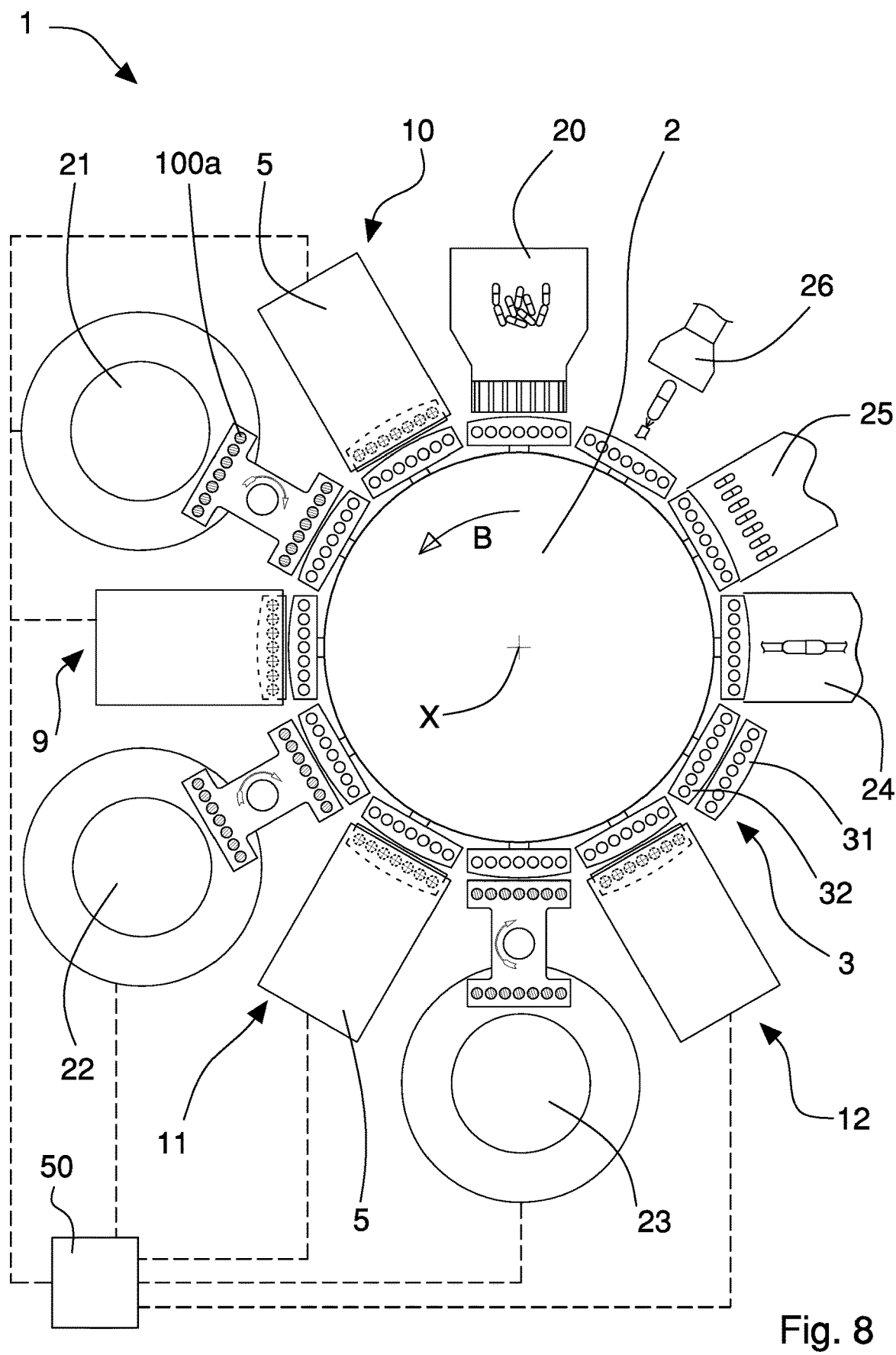
FIG. 8 is a plan schematic view from above of a variant of the filling machine of the invention.

FIG. 8 illustrates another variant of the filling machine 1 of the invention which differs from the previously described embodiment in that it comprises a plurality of filling stations 21, 22, 23, for example three, arranged to supply respective different products into the bodies 100*a* of the capsules 100. The filling machine 1 further includes a plurality of weighing stations 9, 11, 12 placed downstream of respective filling stations 21, 22, 23, with reference to the movement direction B, and arranged to measure the weight of the bodies 100*a* filled with different products. The number of weighing stations 9, 11, 12 is equal to the number of filling stations 21, 22, 23.

The filling machine 1 also includes the station of initial weighing 10 which measures the weight of the empty bodies 100*a* and it is thus placed upstream of the filling stations 21, 22, 23 and downstream of the supplying and opening station 20 of the capsules 100. A processing unit 50 is connected to the weighing stations 9, 10, 11 and to the station of initial weighing 10 for receiving data relative to measured weighs and calculate an effective weight of each product dosed in the bodies 100*a* in the filling stations 21, 22, 23. The processing unit 50 is also able to generate a warning signal in case the body 100*a* is non-compliant i.e. it contains an amount of product having a weight outside the admitted tolerance field.

The exit station 25 is connected to the operative unit 50 for receiving from the latter the warning signal and leave the non-compliant capsules on the movement device 2. The discard station 26, provided downstream of the exit station 25, removes the non-compliant capsules from the movement device 2.

The filling stations 21, 22, 23 are connected to the processing unit 50 to receive therefrom the warning signal and stop such as to interrupt the filling of further capsules 100 which would result to be non-compliant.

In the filling machine 1 of the invention, thanks to the weighing stations 9, 11, 12 placed directly downstream of the filling stations 21, 22, 23, it is possible to immediately detect anomalies in the filling of capsules 100, i.e. possible malfunction of filling stations 21, 22, 23—highlighted by weight measurements outside the admitted tolerance range—and therefore interrupt the filling with products, such as to reduce the number of non-compliant capsules to be discarded.

In this version also of the filling machine 1, thanks to the transfer means 6 and the gripping elements 7 included in each of the weighing stations 9, 10, 12, it is possible to transfer rapidly, simply and efficiently bodies 100a from/to the movement device 2 and weigh precisely and accurately through load cells 4, directly connected to the gripping elements 7, the bodies 100a, empty and containing the different products.

The first transfer elements 16 and second transfer elements 18 of the transfer means 6 are in fact moved along the direction of extraction A with short-length stroke between the various operative positions P1-P4, which can be carried out very quickly. Therefore, the time required to carry out the whole weighing operation in the different weighing stations 9, 10, 11, 12 is very short and can be equal to the duration of stop intervals of an intermittent motion of the filling machine 1 having high rate or speed or productivity. Therefore the filling machine 1 of the invention carries out a total weight control of capsules 100 even at high operative speeds.

The invention claimed is:

1. A filling machine for filling capsules with at least one product, each capsule having a body and a cap, the filling machine comprising:
   a plurality of operative stations for carrying out operations on said capsules;
   a movement device provided with a plurality of supports with respective seats for housing and moving said capsules in sequence through said operative stations; and
   at least one weighing station to weigh at least bodies of said capsules, said at least one weighing station comprising a weighing unit and a transfer system to transfer at least said bodies from said movement device to said weighing unit and vice versa,
   wherein said weighing unit comprises at least one gripping element connected to a respective weighing cell of said weighing unit and provided with a housing configured for receiving and holding by force coupling at least one body to be weighed, and
   wherein said transfer system is moveable along a direction of extraction and includes a first transfer element arranged to remove said at least one body from a respective first seat of said movement device and insert the body into said housing to allow said weighing cell to measure the weight of said body, and a second transfer element to remove said at least one body from said housing and insert said at least one body into the respective first seat of said movement device, after the weight of said body is measured.

2. The filling machine according to claim 1, wherein said first transfer element and said second transfer element are moveable along said direction of extraction between a first operative position, wherein said transfer elements are disengaged and spaced apart from said at least one body and said at least one body is housed in the respective first seat of said movement device such as not to interfere with the movement of said movement device, a second operative position, wherein said first transfer element has completely extracted said at least one body from said first seat and has inserted said at least one body inside said housing of the gripping element, a third operative position, wherein said transfer elements are disengaged and spaced apart from said at least one body housed and hold by force or interference in said housing so that said weighing cell can measure the weight of said at least one body, and a fourth operative position, wherein said second transfer element has completely extracted said at least one body from said housing and has inserted said at least one body inside the respective first seat of said movement device.

3. The filling machine according to claim 1, wherein said weighing unit with said at least one gripping element is arranged above said movement device, and said housing has a lower opening that enables said transfer system to insert in, or extract from, said housing said at least one body along said direction of extraction.

4. The filling machine according to claim 1, wherein said first transfer element has an elongated shape and is arranged to be inserted, when moved along said direction of extraction, inside a respective first seat of said movement device to abut onto a lower portion of at least one body and push said at least one body outside said first seat and inside said housing.

5. The filling machine according to claim 1, wherein said second transfer element has an elongated shape and has at least one terminal end adapted to abut onto an upper portion of said at least one body in order to push said at least one body outside said housing and inside said first seat.

6. The filling machine according to claim 5, wherein said gripping element has at least one lateral opening for inserting and sliding said terminal end of said second transfer element inside said housing and along said direction of extraction.

7. The filling machine according to claim 1, wherein said housing extends longitudinally, and is convergent starting from a lower opening arranged for the insertion and extraction of said at least one body, and towards said weighing cell, an internal cross-section of said housing progressively funneling from said lower opening to a smaller dimension of an external transverse dimension of said at least one body so as to receive and hold said at least one body by force or interference coupling.

8. The filling machine according to claim 1, wherein said plurality of operative stations comprises at least one filling station arranged to dispense a product into the bodies of said capsules, and said weighing station is placed downstream of said filling station, with reference to a movement direction of said capsules in said filling machine, to measure the weight of said bodies containing said product.

9. The filling machine according to claim 8, comprising a station of initial weighing provided with a respective weighing unit and with respective transfer system and placed upstream of said filling station, with reference to said movement direction, to measure the weight of said empty bodies.

10. The filling machine according to claim 9, comprising a processing unit connected to said weighing station and to said station of initial weighing and configured to receive data about the measured weights, calculate an effective weight of the product dosed in each capsule and generate a warning signal in case of a non-compliant capsule.

11. The filling machine according to claim 1, wherein said plurality of operative stations comprises a plurality of filling stations arranged to supply respective products in the bodies of said capsules, a plurality of weighing stations placed downstream of the respective filling stations, with reference to said movement direction, and configured to measure the weight of said bodies filled with said products, and a station of initial weighing placed upstream of said filling stations to measure the weight of said empty bodies.

12. The filling machine according to claim 1, wherein said movement device comprises a carousel rotating about a vertical rotation axis and provided with said plurality of supports, placed angularly spaced apart along a circumferential rim of said carousel.

* * * * *